(12) United States Patent
Sinensky et al.

(10) Patent No.: US 8,592,551 B2
(45) Date of Patent: Nov. 26, 2013

(54) BIOMOLECULAR RECOGNITION OF CRYSTAL DEFECTS

(75) Inventors: Asher K. Sinensky, Somerville, MA (US); Angela M. Belcher, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1062 days.

(21) Appl. No.: 11/912,043

(22) PCT Filed: Oct. 19, 2005

(86) PCT No.: PCT/US2005/037975
§ 371 (c)(1),
(2), (4) Date: Nov. 12, 2008

(87) PCT Pub. No.: WO2006/045071
PCT Pub. Date: Apr. 27, 2006

(65) Prior Publication Data
US 2009/0305226 A1 Dec. 10, 2009

Related U.S. Application Data

(60) Provisional application No. 60/620,386, filed on Oct. 19, 2004.

(51) Int. Cl.
*A61K 38/00* (2006.01)
*A61K 39/00* (2006.01)

(52) U.S. Cl.
USPC ............................ 530/300; 530/328; 530/333

(58) Field of Classification Search
None
See application file for complete search history.

(56) References Cited

U.S. PATENT DOCUMENTS

| | | | |
|---|---|---|---|
| 5,357,041 A * | 10/1994 | Roberts et al. | 530/326 |
| 5,620,843 A * | 4/1997 | Hellings et al. | 435/5 |
| 5,869,350 A | 2/1999 | Heeger et al. | |
| 6,099,823 A | 8/2000 | Falb | |
| 6,361,944 B1 | 3/2002 | Mirkin et al. | |
| 2003/0068900 A1 | 4/2003 | Belcher et al. | |
| 2003/0113714 A1 | 6/2003 | Belcher et al. | |
| 2003/0181423 A1* | 9/2003 | Clapper et al. | 514/100 |

FOREIGN PATENT DOCUMENTS

| WO | WO 03/026590 A2 | 4/2003 |
|---|---|---|
| WO | WO 03/029431 A2 | 4/2003 |
| WO | WO 2004/033488 A2 | 4/2004 |

OTHER PUBLICATIONS

Whaley et al. 2000.*
Alivisatos et al., "Organization of 'nanocrystal molecules' using DNA," Nature, Aug. 15, 1996, 382:609-611.
Barbas et al., Eds., Phage Display: A Laboratory Manual, 2001, "Protocol 15.6, Spectrophotometric Quantitation of Phage," 15.17-15.18.
Belcher et al., "Control of crystal phase switching and orientation by soluble mollusk-shell proteins," Nature, May 2, 1996, 381:56-58.
Cha et al., "Biomimetic synthesis of ordered silica structures mediated by block copolypeptides," Nature, Jan. 20, 2000, 403:289-292.
Colace et al., "Efficient high-speed near-infrared Ge photodetectors integrated on Si substrates," Applied Physics Letters, Mar. 6, 2000, 76(10):1231-1233.
Deegan et al., "An X-ray photoelectron spectroscopy study of the HF etching of native oxides on Ge(111) and Ge(100) surfaces," Applied Surface Science, 1998, 123/124:66-70.
Flynn et al., "Synthesis and organization of nanoscale II-VI semiconductor materials using evolved peptide specificity and viral capsid assembly," J. Mater. Chem., 2003, 13:2414-2421.
Gan et al., "Characterization of dislocations in germanium substrates induced by mechanical stress," Applied Physics Letters, Aug. 24, 1998, 73(8):1068-1070.
Giovane et al., "Correlation between leakage current density and threading dislocation density in SiGe *p-i-n* diodes grown on relaxed graded buffer layers," Applied Physics Letters, Jan. 22, 2001, 78(4):541-543.
Kruml et al., "A transmission electron microscopy in situ study of dislocation mobility in Ge," J. Phys.: Condens. Matter, 2002, 14:12897-12902.
Lee et al., "Ordering of Quantum Dots Using Genetically Engineered Viruses," Science, May 3, 2002, 296:892-895, USA.
Luan et al., "High-quality Ge epilayers on Si with low threading-dislocation densities," Applied Physics Letters, Nov. 8, 1999, 75(19):2909-2911.
Mao et al., "Viral assembly of oriented quantum dot nanowires," PNASA, Jun. 10, 2003, 100(12):6946-6951.
Mao et al., "Virus-based toolkit for the directed synthesis of magnetic and semiconducting nanowires," Science, 2004, 303:213-217.
Mirkin et al., A DNA-based method for rationally assembling nanoparticles into macroscopic materials, Nature, Aug. 15, 1996, 382:607-609.
Office Action mailed May 2, 2011, in corresponding Japanese Application No. 2007-538085, five pages, with English translation, 7 pages.
Rosner et al., "Cathodoluminescence mapping of epitaxial lateral overgrowth in gallium nitride," Applied Physics Letters, Apr. 5, 1999, 74(14):2035-2037.
Seeman et al., "Emulating biology: Building nanostructures from the bottom up," PNAS, Apr. 30, 2002, 99(Suppl.2):6451-6455.
Thai et al., "Identification and Characterization of $Cu_2O$- and ZnO-Binding Polypeptides by *Escherichia coli* Cell Surface display: Toward an Understanding of Metal Oxide Binding," Biotechnology and Bioengineering, 2004, 87(2):129-137.
Whaley et al., "Selection of Peptides with Semiconductor Binding Specificity for Directed Nanocrystal Assembly," Nature, Jun. 8, 2000, 405:665-668, USA.
Whitesides et al., "Self-assembled monolayers and lithography," The Robert A. Welch Foundation 39th Conference on Chemical Research Nanophase Chemistry, Oct. 23-24, 1995, 109-121.
International Search Report dated Jun. 14, 2006, in corresponding PCT/US05/37975, 1 page.

* cited by examiner

*Primary Examiner* — Cecilia J. Tsang
*Assistant Examiner* — Li Lee
(74) *Attorney, Agent, or Firm* — Foley & Lardner LLP

(57) ABSTRACT

Discrete and diffuse defects in a surface are detected. Discrete defects that may compromise the performance may be repaired.

20 Claims, 5 Drawing Sheets

BIOMOLECULAR RECOGNITION OF CRYSTAL DEFECTS

The present application claims priority under 35 U.S.C.§120 to international PCT application PCT/US2005/037975, filed Oct. 19, 2005, which claims priority under 35 U.S.C.§119(e) to U.S. provisional patent application U.S. Ser. No. 60/620,386, filed Oct. 19, 2004, each of which is incorporated herein by reference in its entirety.

FIELD OF THE INVENTION

This application relates to the use of biological mechanisms to recognize inhomogeneities in material surfaces.

BACKGROUND OF THE INVENTION

Defects form in materials through a variety of mechanisms and can dramatically affect the performance of those material. Crystal defects such as vacancies are inherent in metals and semiconductors and affect conductivity and other properties. Dislocations and grain boundaries form where there are interruptions to the periodicity of crystalline structures. Larger defects, such as cracks, or chemical defects, such as variations in the composition of a material, also affect the everyday performance of the material and can also lead to dramatic failures. Specificity is a hallmark of biological interactions. In natural systems, biomolecules are able to differentiate individual target molecules from thousands of competitors. Mimicking this specificity represents a challenge in some inorganic systems where the target is diffuse and inseparable from a large, competing background. Thus, it is desirable to exploit the specificity of biological interactions to detect defects and other inhomogeneities in a surface before the material is put into service or before it fails while in service.

SUMMARY OF THE INVENTION

In one aspect, the invention is a method of repairing a defect in a surface coating on a substrate. The method includes providing a material comprising a moiety exhibiting an affinity for the substrate but not for the coating; a repair material for the coating, and a tether linking the moiety and the repair material, using the material to deliver the repair material to the defect, and incorporating the repair material into the surface coating.

The substrate may include a metal, ceramic, polymer, or semiconductor. The repair material may be a catalyst for electroless plating, and incorporating may include plating at least the defect with the surface coating material. The repair material may be an oligomer of a polymer component of the surface coating, and incorporating may include heating the region of the defect, exposing the region of the defect to a cross-linking agent, or both. The repair material may include a particle of the material of the surface coating, and incorporating may include annealing the region of the defect. The moiety may be a peptide, and the tether may include a peptide, streptavidin, or a nucleic acid oligomer.

In another aspect, the invention is a composition comprising one or more peptides. The one or more peptides are selective for a target feature of a material having a predetermined composition with respect to a material having substantially the same composition but lacking the target feature.

The material may be polycrystalline, and the target feature may be grains having a predetermined orientation or the grain boundaries. The material may be crystalline, and wherein the target feature may be a dislocation. The material may be an alloy or mixture of two or more metals or ceramics, and the target feature may be grains having a predetermined equilibrium or non-equilibrium composition. The material may be a semiconductor material, and the target feature may be a doped semiconductor material. The material may be a composite of a matrix and a reinforcement material, and wherein the target feature may be the reinforcement material. The material may be a corrosion scale having a predetermined composition and the target feature may be a scale having a different composition. The material may be an optionally passivated metal and the target feature may be a corrosion pit. The material may be a coating on a substrate and the target feature may be the substrate material.

The one or peptides may be part of a virus. The peptide may be linked to a fluorescent, radioactive, or magnetic label. The material is single crystalline germanium, the target feature is a screw dislocation, and the peptide may have the sequence CTSPHTRAC (Seq ID: 2).

In another aspect, the invention is a method of detecting a target feature on a sample. The method comprises providing a composition comprising one or more peptides, wherein the one or more peptides are selective for the target feature in a material having a predetermined composition with respect to a material having substantially the same composition but lacking the target feature, preparing at least a portion of a surface of the sample, disposing the composition on the portion under conditions where the peptides will bind the target feature if it is present in the portion, removing the composition from the portion while leaving the bound peptides behind, and detecting the bound peptides.

The composition may be a solution in a carrier solvent. Preparing may include one or more of cleaning with a detergent, cleaning with a solvent, etching, polishing, and removing an oxide. Disposing may include spraying a solution of the composition on the surface. Removing may include rinsing the portion with a solvent, for example, an aqueous solvent, optionally including a detergent, bovine serum albumin, or both. The one or peptides may be part of a virus, and the composition may be a suspension of the virus, for example, with a concentration of from about $10^7$ to about $10^{12}$ virus/µL. Detecting may include one or more of photographing the sample, measuring a magnetic field of the sample, detecting radiation emitted by the sample, and detecting fluorescence from the sample.

In another aspect, the invention is a method of identifying a peptide sequence for use in detecting a feature of a surface. The method may include the steps of:

A) providing a first selection of peptides;

B) exposing the first selection of peptides to a surface exhibiting a first surface characteristic and a first surface density of a second surface characteristic so that at least a portion of the peptides may bind to the surface;

C) recovering the bound peptides from the surface;

D) exposing a second selection of peptides having the same sequences as the bound peptides to a surface exhibiting the first surface characteristic and a second surface density of the second surface characteristic, wherein the second density is less than the first density, so that at least a portion of the peptides from the second selection will not bind to the surface; and E) recovering the unbound peptides.

The method may further include:

F) exposing a third selection of peptides having the same amino acid sequence as the unbound peptides to the surface exhibiting first and second surface characteristics so that at least a portion of the peptides from the third selection may bind to the surface; and G) recovering the bound peptides.

The medium used in step C may differ from a medium used in step G in one or more of a concentration of a component, a pH, and the presence or absence of a component. The second surface density may be about zero. The method may further include repeating step B with a selection of peptides having the same sequences as the bound peptides. The selection of peptides having the same sequences as the bound peptides may include the recovered bound peptides. The method may further include repeating steps B-E using a selection of peptides having the same sequences as the unbound peptides as the first selection of peptides. The selection of peptides having the same sequences as the unbound peptides may include the recovered unbound peptides. Step A comprises providing a phage display library including the first selection of peptides. The phage display library may exhibits a variation in the pIII coat protein or the pVIII coat protein of M13 phage. The method may further include amplifying the bound peptides after step C, amplifying the unbound peptides after step E, or both. The second selection of peptides may include the recovered bound peptides. The method may further include comparing the affinity of the unbound peptides for a surface exhibiting both the first and second surface characteristics and a surface exhibiting the first surface characteristic but not the second surface characteristic. The method may further include comparing the surface characteristics of a surface exhibiting the first and second surface characteristics and a surface exhibiting the first surface characteristic but not the second characteristic.

In another aspect, the invention is a composition comprising one or more peptides, wherein the sequences of the peptides are selected by a process including the steps of:

A) providing a first selection of peptides;

B) exposing the first selection of peptides to a surface exhibiting a first surface characteristic and a first surface density of a second surface characteristic so that at least a portion of the peptides may bind to the surface;

C) recovering the bound peptides from the surface;

D) exposing a second selection of peptides having the same sequences as the bound peptides to a surface exhibiting the first surface characteristic and a second surface density of the second surface characteristic, wherein the second density is less than the first density, so that at least a portion of the peptides from the second selection will not bind to the surface; and E) recovering the unbound peptides.

The method may further include:

F) exposing a third selection of peptides having the same amino acid sequence as the unbound peptides to the surface exhibiting first and second surface characteristics so that at least a portion of the peptides from the third selection may bind to the surface; and G) recovering the bound peptides.

In an alternative embodiment, the method may further include F) comparing the affinity of the unbound peptides for a surface exhibiting both the first and second surface characteristics and a surface exhibiting the first surface characteristic but not the second surface characteristic.

In an alternative embodiment, the method may further include F) comparing the surface characteristics of a surface exhibiting the first and second surface characteristics and a surface exhibiting the first surface characteristic but not the second characteristic.

The method may further include amplifying the bound peptides after step C, amplifying the unbound peptides after step E, or both.

BRIEF DESCRIPTION OF THE DRAWING

The invention is described with reference to the several figures of the drawing, in which.

DETAILED DESCRIPTION OF CERTAIN PREFERRED EMBODIMENTS

Figure 1:
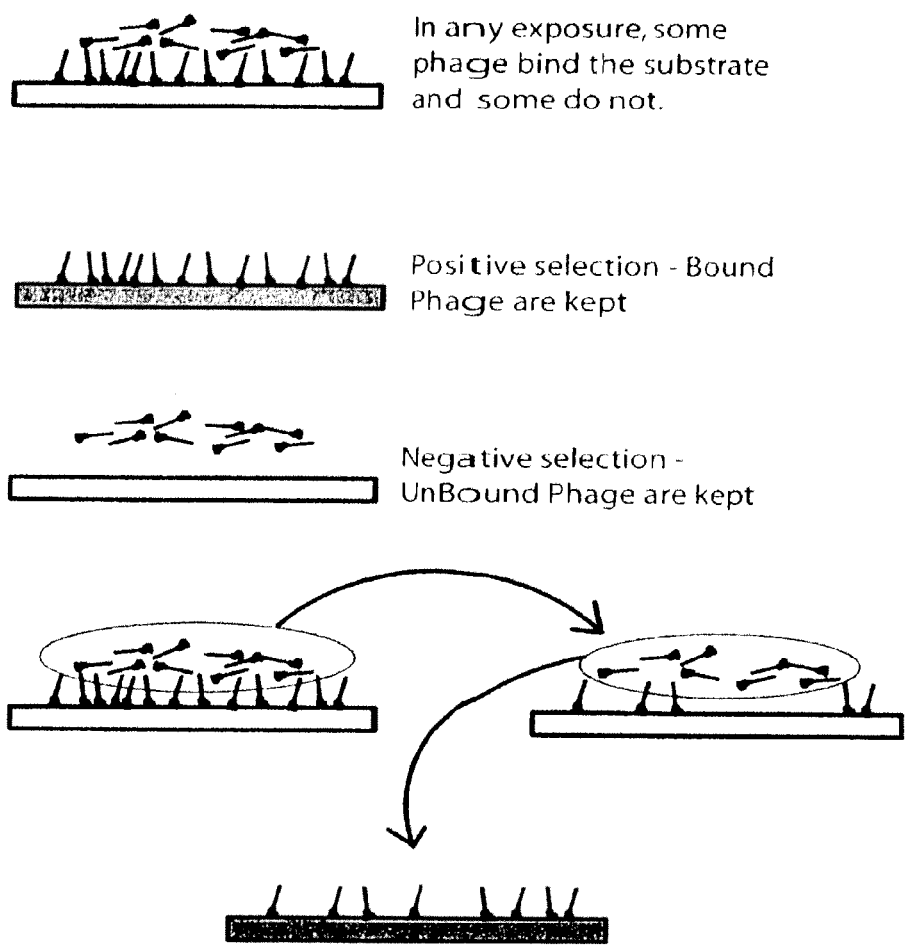
FIG. 1 is a schematic illustrating an exemplary biopanning protocol for identifying phage that are selective for a particular surface feature

In the past decade, considerable progress has been made in the understanding of how biological molecules interact with inorganic materials. Biomolecules have been used to influence the phase[1], growth[1-3] and organization[4-7] of inorganic materials in ways that may provide a glimpse into the future of self-assembly. In the case of semiconducting materials, phage display using the filamentous M13 virus has played a crucial role in identifying peptides that have binding affinity and specificity[8] for a chosen substrate. However, there is a class of problems in which challenges arise because the selection target is diffuse and inseparable from a large competing background. This inseparability complicates selection processes in which it is desirable to isolate the selection target.

Two examples of such inseparable/diffuse targets are surface defects (dislocations, step edges, grain boundaries) and impurities (intentional or otherwise). It is difficult to isolate the surface defect during the selection. The ability to bind defects provides a path to potential applications. In systems where defect distribution can be controlled (e.g. epitaxial lateral overgrowth[9]), defect binding can be used to direct templated assembly. In addition, in any system where defect density influences functionality (e.g. leakage current[10], strain hardening) it is useful to be able to locate defects in a non-destructive manner.

Phage display is a combinatorial technique in which a library of viruses expressing random peptide sequences is exposed to a substrate of interest. In some embodiments, the random library includes roughly $10^{11}$ viruses that have each been uniquely modified, representing $10^9$ variations. The modification may take the form of an additional amino acid sequence which is expressed on one of the coat proteins of the viral assembly. In one embodiment, the phage library is based on the M13 bacteriophage expressing a modification on one of the coat proteins, e.g., pVIII or pIII. M13 is a filamentous phage (~880 nm long and 6 nm in diameter) with a capsid including roughly 2700 copies of coat protein pVIII. In an exemplary phage display library, five copies of the modified pIII protein are expressed at one end of the viral assembly. Alternatively, the modification is made to pVIII. Several rounds of selection, called biopanning (see U.S. Patent Publications Nos. 2003006890 and 20030113714, the contents of both of which are incorporated herein by reference, are used to identify those sequences that selectively bind to the substrate of interest. Other viruses, such as f1, fd, and tobacco mosaic virus (TMV) may also be employed in embodiments of the invention.

As used herein, the term "peptide" denotes a string of at least two amino acids linked together by peptide bonds. Peptide may refer to an individual peptide or a collection of peptides. Peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired activity of the peptide.

In the first round of selection, the random phage library is exposed to a substrate of interest for an hour or some other suitable period of time. After exposure, the substrate is washed, for example, with Tris-buffered saline or phosphate buffered saline, to remove unbound phage. The bound phage are eluted by decreasing the pH, for example, using a buffer such as glycine HCl, which has a pH of about 2. This eluted population of phage has a decreased genetic diversity compared to the original population because only a portion of the expressed peptide fusions shows an affinity for the substrate. The eluted population may be amplified using their natural bacterial host and purified using selective precipitation. This new 'library' is then exposed to the substrate again and the process is repeated. In different rounds of selection, the wash may be made more or less aggressive. For example, the wash may be made more aggressive by increasing the concentration of a detergent such as Tween-20™ or other commercially available surfactant, e.g., Triton brand surfactants, available from Dow, or by introducing a competitive binder such as bovine serum albumin (BSA), thus selecting only the sequences that show strong affinity for the substrate. The concentration of Tween-20 or BSA may be arbitrarily high. However, in some embodiments, concentrations of greater than 0.5% Tween-20 may render the wash solution soapy and more difficult to manage, and concentrations of BSA greater than 0.5 g/L may compete too strongly with binding to the substrate. After several rounds, the viral DNA can be sequenced, revealing the modified amino acid sequences that have exhibited an affinity for the surface.

FIG. 1 exhibits a variation on this technique for use in developing a population of phage that are selective for a particular target feature, a difference in a surface property between two otherwise substantially identical substrates. In the first instance, the phage library is exposed to a substrate that exhibits the target feature. In some embodiments, the target feature is a variation of some "background" property of the surface. For example, the substrate may be a single crystal material, for example, epitaxial germanium, and the target feature may be the emergence of screw dislocations at the surface. Alternatively, the target feature may be regions of p- or n-type silicon in an undoped silicon surface. In another embodiment, the surface is a multigrained alloy or ceramic and the target feature is the grain boundaries. Alternatively, the target feature may be grains in an alloy that have a particular composition, e.g. $\alpha$ grains in an $\alpha+\beta$ mixture. In superconducting tapes, e.g., the orientation of the grains affects the performance of the material, and the target feature may be grains having a suboptimal orientation. In composites, the target feature may be defined by delamination of the matrix and reinforcement phases, and the phage may selectively bind the delaminated regions where the reinforcement phase is exposed. Alternatively, the phage may selectively bind corrosion products, for example, corrosion pits in metals, or areas where corrosion scale having a different composition from the remainder of the scale forms after spalling, e.g., because of depletion of an alloying element in the underlying metal.

Where the target feature is discrete rather than diffuse, biopanning may be performed with two "pure" surfaces, one exhibiting the target feature and the other exhibiting the background feature. For example, where the target feature is $\alpha$ grains, two surfaces may be prepared, one with the $\alpha$ composition and the other with the $\beta$ composition. Positive selection is performed on the $\alpha$ sample and negative selection is performed on the $\beta$ sample. An alloy sample may be used to confirm the selectivity of phage displaying the particular peptide that results from the selection. Likewise, an entire sample may be formed from p- or n-type silicon and biopanning performed with positive selection on the doped silicon and negative selection on undoped silicon. This technique may also be used to locate defects in coatings on materials. Negative selection is performed on a sample of the coating material, while positive selection is performed on a sample of the substrate that will be coated. For example, the substrate material may be silicon, and the coating material may be tantalum nitride or gold. Nickel and chromium are plated on plastics and metals to create corrosion-resistant coatings. Likewise, oxides are frequently grown on metal substrates to provide particular surface properties and to control the corrosion of the material. In this example, negative selection is performed on the oxide, while positive selection is performed on the substrate material. The substrate material may be any material that is being coated, e.g., a metal, ceramic, semiconductor, or polymer.

Alternatively or in addition, these techniques may be adapted to locate pinholes in polymer coatings. Polymerized phenylenevinylene coatings are used as conductive polymers in LEDs (see U.S. Pat. No. 5,869,350, the contents of which are incorporated herein by reference). Other conductive polymers, such as polypyrrole and polyaniline, are also employed as conductive coatings. Polyimides may be used as the dielectric layer in both semiconductors and thin film multichip modules. Other polymers that find uses in semiconductor applications include but are not limited to acrylics, polyesters, polystyrenes, allylic polymers, epoxies, polyurethanes, silicones, polysulfones, and phenolics. In use, these may be deposited directly onto a silicon surface, a dielectric, a semiconductor material, e.g., germanium, gallium arsenide, gallium nitride, zinc selenide, cadmium sulfide, or a conductive lead. It may be desirable to identify several peptide sequences that are selective for each material that is being coated with respect to the coating material.

Practically any surface may be biopanned with the phage display library so long as it can be suitably prepared. Appropriate surface preparation techniques will depend on the composition of the surface and the nature of the target feature. For example, a polymer or polymer matrix composite surface may only need to be cleaned to remove surface dirt. Likewise, some ceramic surfaces may also only require cleaning. Appropriate cleaning agents may include detergents and mild solvents. Metallic and semiconductor surfaces may need to be etched to remove a passivating layer. Depending on how long it takes the metal surface to passivate, it may be desirable to perform the biopanning in an inert atmosphere. For example, silicon forms a passive oxide layer in about an hour, while a similar layer requires about a month to develop on germanium. Alternatively, if the oxidation behavior of the material is known, biopanning may be performed on the passivation layer to identify, for example, the approximate composition of the underlying material. For example, the passive layer on stainless steel is predominantly chromia. To identify corrosion pits, it may not be necessary to find a peptide sequence that can distinguish stainless steel and iron oxide but rather one that preferentially binds iron oxide instead of chromia, obviating polishing the surface to remove the passive oxide layer. To distinguish dislocations, grain boundaries, and other crystal defects, it may be desirable to polish the surface to remove scratches. Alternatively, materials may be cleaved to reveal a clean surface.

Thus, the phage that are eluted from the surface exhibit an affinity for the surface including the target feature. The first selection is a positive selection, which samples the whole surface without built-in discrimination for certain surface features. To identify phage selective for a particular feature, after a round of positive selection is complete, a round of negative selection is performed on a surface that exhibits the predefined background property but not the target feature. For example, the surface for the negative selection may be melt-grown single crystal germanium or an a alloy in the embodiments described above. This is a negative selection step, and the phage that do not bind to the surface are recovered and amplified. In the negative selection, the surface is essentially being used as a filter for sequences that exhibit an affinity for the background property but not the target feature. The use of both positive and negative selection steps provides a way to discriminate between surfaces that do or do not exhibit a particular target feature. The positive selection step is then repeated, with the phage exposed to the surface exhibiting the target feature and those phage that bind to the surface eluted and recovered. The recovered phage may be amplified after any of the selection steps.

The positive and negative selection steps may be repeated, either alternating with one another or in blocks (e.g., with the positive selection step repeated one or more times before one or more negative selection steps). The aggressiveness of the elution medium may be adjusted as well. Where a buffered acidic solution is used to elute the phage, lowering the pH will render elution more aggressive. Dilution of the solution will render the elution less aggressive. The aggressiveness of the elution medium for the negative selection steps may be adjusted independently of those for the positive selection steps. In some embodiments, it may be desirable to increase or decrease the selectivity of a particular selection step.

Once a particular peptide sequence has been identified, the selectivity may be further refined by modifying the peptide in various ways. For example, peptides may be produced with D amino acids, or various chemical entities may be added to the peptides. The selectivity of these modified peptides with respect to the target feature may be compared side by side or in larger samples.

The phage population that results from the biopanning process displays a peptide that has an affinity for the target feature in preference to the other features of a particular surface. After selection is complete, it may be desirable to verify that the peptide does selectively bind the target feature (as opposed to some other feature of the surface) and that the target feature is the dominant property that distinguishes the surfaces used to make the selection. A population of phage that exhibit this peptide sequence may be used in the field to detect the same target feature on the same kind of surface, e.g., in a manufacturing setting or after the material has been in use for some time. For example, solutions of, for example, about $10^7$ to about $10^{12}$ phage/µL of phage may be sprayed or washed on semiconductor substrates or superconducting tapes to detect crystalline defects. The phage may also include a fluorescent tag for easy detection. For example, the phage may be fluorescently tagged using an antibody for the phage (biotinylated anti-fd) which is linked to a fluorescent dye (e.g., streptavidin conjugated tetramethylrhodamine—TMR) via the biotin-streptavidin linkage. If a surface is expected to include different types of target features, different phage populations may be developed through biopanning and the different target features detected by including different color tags on the different populations. Other detection systems, e.g. radiolabeled streptavidin or streptavidin-conjugated gold particles, may be used as well. Where the surface being analyzed is not magnetic, the phage may be labeled with magnetic particles.

The peptide displayed by the phage population may be used without the phage to detect the target feature on a surface. Peptides may be produced using solid phase synthesis methods, for example, using Fmoc based synthesis. A solution of labeled peptides may be sprayed or washed over a surface being characterized. Because a labeled peptide does not exhibit as intense an emission as the phage, which can be multiply labeled, it may be more suitable to use peptides to identify grains or larger inhomogeneities rather that point or line defects. Alternatively, it may be desirable to use a larger concentration of peptide in solution than for a population of phage used in the same application. In another embodiment, the peptide may be conjugated with a receptor for an enzyme such as alkaline phosphatase that can exhibit a more intense emission. In another embodiment, the peptide may be coupled to a particle exhibiting a more intense emission, for example, a quantum dot.

In another embodiment, other display systems may be used to identify the peptide selective for the target feature. For example, other virus display systems, e.g., fl, fd, or tobacco mosaic virus, may be employed. Cell-based display systems may also be employed. For example, peptide display libraries may be prepared with yeast or *E. Coli*. The cell membranes of these materials exhibit a charge in addition to expressing the peptide fusion. In some embodiments, when a peptide is identified using a cell based display method but used without the phage in practice, it may be desirable to produce the peptide with a short polyD or polyE fusion, e.g., 1-5 mers long.

Where a peptide has been identified that is selective for a discrete feature in a surface, it may be desirable to use the peptide to help fix the defect. For example, the peptide may be conjugated, via a phage or other linker, to a coating material. The peptide can localize the coating material to the pinhole or other defect, and then the material may be processed to incorporate the delivered material into the coating. For example, the peptide may be linked to an oligomer chain of the material of a polymer coating. Once in place, the coating may be heated above a Tg of the polymer to allow the oligomer chain to entangle itself with the surrounding coating. Alternatively, the coating may be exposed to a cross-linking agent, e.g., UV light, to chemically link the oligomer to the surrounding polymer. Where a metallic coating is employed, the peptide may be linked to a particle of the coating material. After the particle is delivered to the defect site, the coating may be annealed briefly. Alternatively or in addition, the repair material may be a catalyst for electroless plating. Once the repair material is delivered to the defect, the plating method is performed according to techniques known to those skilled in the art. Since the catalyst is localized, the defect is the primary region that is "plated," filling in the defect without significantly adding to the thickness of the plating layer. Where heat is used to increase the continuity between the delivered material and the coating, it may be desirable that the substrate be resistant to the particular temperature or that the heating time be brief. For example, where a coating is heated on a polymer substrate, it may be desirable that the temperature be less than the Tg or Tm of the substrate material.

The peptide that is used to locate the defect may be linked to the repair material using linking techniques known to those skilled in the art. For example, the peptide and the repair material may both be biotinylated, and a bifunctional streptavidin tether used to link the two materials. It may be desirable to attach, to the selective peptide, a peptide sequence that can receive the biotin without interfering with the ability of the selective peptide to locate the defect. Alternatively, a poly-N nucleotide sequence may be attached to the peptide, e.g., using techniques in Hermanson, G T., *Bioconjugate Techniques*, San Diego: Academic Press, 1996, the contents of which are incorporated by reference. The repair material may then be conjugated with the complementary sequence, following which the two sequences are hybridized to link the selective peptide and the repair material. Likewise, oligomers of a polymeric repair material may simply be functionalized with the complementary sequence using chemical reactions known to those skilled in the art. Techniques for preparing nucleotide-functionalized metal particles are also well described in the art, for example, in U.S. Pat. No. 6,361,944, the contents of which are incorporated herein by reference. In one embodiment, oligonucleotides are prepared with an alkanethiol at the 3' or 5' terminus. Such nucleotide-thiol complexes readily attach to many metals, including gold and nickel. See Whitesides, Proceedings of the Robert A. Welch Foundation 39th Conference On Chemical Research Nanophase Chemistry, Houston, Tex., pages 109-121 (1995).

Alternatively or in addition, peptides may be conjugated to a metallic repair material. Peptides that exhibit an affinity for the repair material may be incubated with particles of the repair material in solution. For example, dilute solutions of nanoparticles (e.g., 0.05-3 nM) may be combined with peptide or a peptide solution to form a solution with about 1-2 mM peptide. The peptide that is selective for the substrate with respect to the coating material may be fused to the peptide that exhibits an affinity for the repair material. The bifunctional peptide may be coordinated to the repair material and then used to deliver the repair material to the defect.

EXAMPLES

Example 1

Locating Threading Dislocations on (100) Ge-on-Si

We used biopanning to identify phage selective for threading dislocations in (100) germanium. There are two advantages to the use of germanium for this selection. Germanium oxidizes slowly[11], so a clean surface can be created and maintained in a lab setting. In addition, growing epitaxial germanium thin films on silicon (Ge-on-Si) is an effective way to create single crystal, albeit highly defective, germanium substrates. Defects in the Ge-on-Si system have been well studied in the hopes of integrating optical devices with silicon logic[12]. The defects created in the deposition of germanium thin films on silicon are threading dislocations whose density can be partially controlled through processing[13]. Threading dislocations form near the germanium/silicon interface and exit the germanium through the exposed (100) surface. The point where a dislocation emerges at a crystal surface is a localized surface defect with a geometry, reactivity and electronic structure that differs from the rest of the Ge surface. The primary dislocation system in germanium has a Burgers vector with length and direction (a/2) <011>[14,15] (a length of ~4 Å). The two substrates used were Ge-on-Si (unnanealed, high defect density) and a Ge wafer (negligible defect density). The Ge-on-Si substrate is composed of an epitaxially grown thin film of germanium that is approximately one micron thick grown on a silicon wafer. The surface defect density is roughly $10^9/cm^2$ [13]. While this high density would render any solid state device ineffective, it actually impacts only a small percentage of the crystal surface. The distance over which a dislocation significantly affects the geometry of a crystal is on the order of the Burgers vector. For germanium with a dislocation density of $10^9/cm^2$, a Burgers vector of 4 Å implies that roughly 0.0001% of the surface is geometrically influenced by the defects, e.g., the target is diffuse. However, it should be noted that the space charge region associated with the dislocation is on the order of the Debye length (~50 nm in undoped Ge), which can be considerably larger than the Burgers vector.

Identification of Defect Selective Peptide Sequence

We used two types of Ge-on-Si samples to identify selective peptide sequences. Typical dislocation densities for as-grown Ge-on-Si are on the order of $10^9/cm^2$. The dislocation density of Czochralski grown germanium is far lower ($10^3/cm^2$). The phage display kit employed in this work utilizes a 7-amino acid constrained library (New England Biolabs PhDC7C). The term "constrained" indicates that the random amino acid sequence is flanked by cysteines. These cysteines form a disulfide linkage which forces the peptide fusion into a ring-like structure. This limits the conformational freedom of the peptide, thus insuring a more specific fit to the substrate. The protocol described in the PhD-C7C manual, the contents of which are incorporated herein by reference, were used to identify phage that preferentially bind the Ge-on-Si surface. Five selections were performed, as follows:

1) Positive selection on a high density sample, followed by amplification

2) Positive selection on a high density sample using the amplified eluate, followed by amplification 3) Negative selection on a low density sample (e.g., eluting the non-binding phage), without amplification 4) Negative selection on a low density sample without amplification 5) Positive selection on a high density sample.

Figure 2:
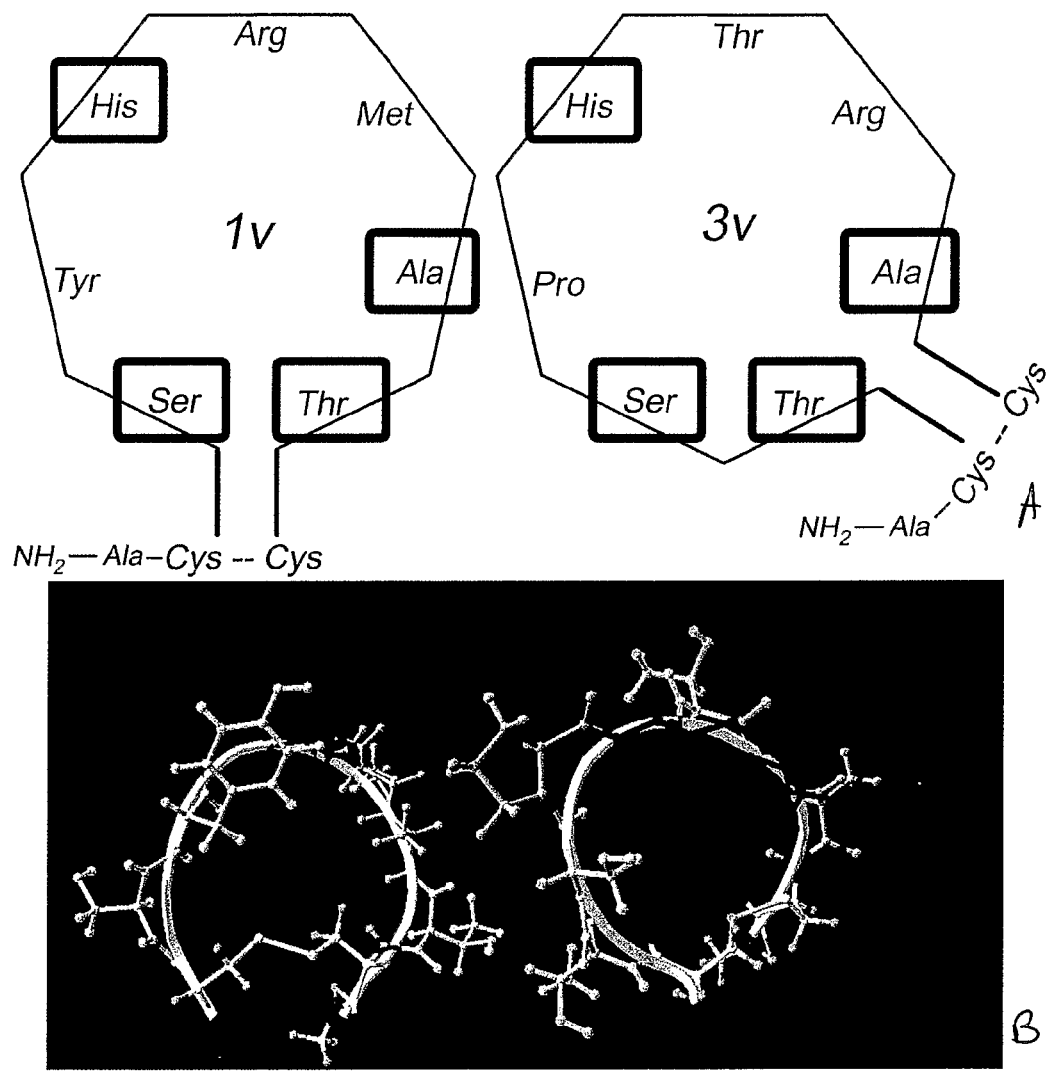
FIG. 2A is a schematic diagram of two peptide sequences expressed by engineered M13 that were identified by biopanning for phage that are selective for Ge-on-Si surfaces.
FIG. 2B is a Monte Carlo simulation of the two peptides illustrated in FIG. 2A.

This yielded two consensus sequences, CSYHRMATC (Seq ID: 1) and CTSPHTRAC (Seq ID: 2). These sequences are quite similar, especially when the cyclic nature of the sequence is considered (FIG. 2). The first sequence was named sequence 1v and the second 3v. These sequences occurred with similar frequency. The specificity of the sequences for the high dislocation surface was then determined. 5 mm squares of the high and dislocation density samples were rinsed in DI water and dipped in 40% HF for 10 sec three times with water rinses in between. The samples were rinsed twice with acetone, twice with ethanol and once again with acetone. A solution of $10^{10}$ plaque forming units (pfu) was prepared in 90 μl of Tris-buffered saline (TBS) with 0.2% Tween-20 (TBST), and a 20 μl drop of this solution placed on each sample. Samples were allowed to set for 1 hour in a clear plastic box, following which they were rinsed with TBST+0.5 g/L of BSA, followed by two rinses with 10% TBS. The samples were then exposed to a solution of 0.01 mM Glycine-HCl+0.1M NaCl for 1 to 5 minutes and rinsed twice with 10% TBS. The phage was eluted with 0.2M Glycine-HCl, which was then neutralized with Tris-HCl. This final solution was then titrated to determine the activity of the bound phage. Sequence 1v exhibited no notable specificity, but sequence 3v exhibited 90× greater binding on the high density samples with respect to the low density samples. Control samples tested with wild-type M13KE phage showed no specificity for either the high or low density samples.

Example 2

Characterization of Peptide Sequence Interactions with Substrate

Figure 3:
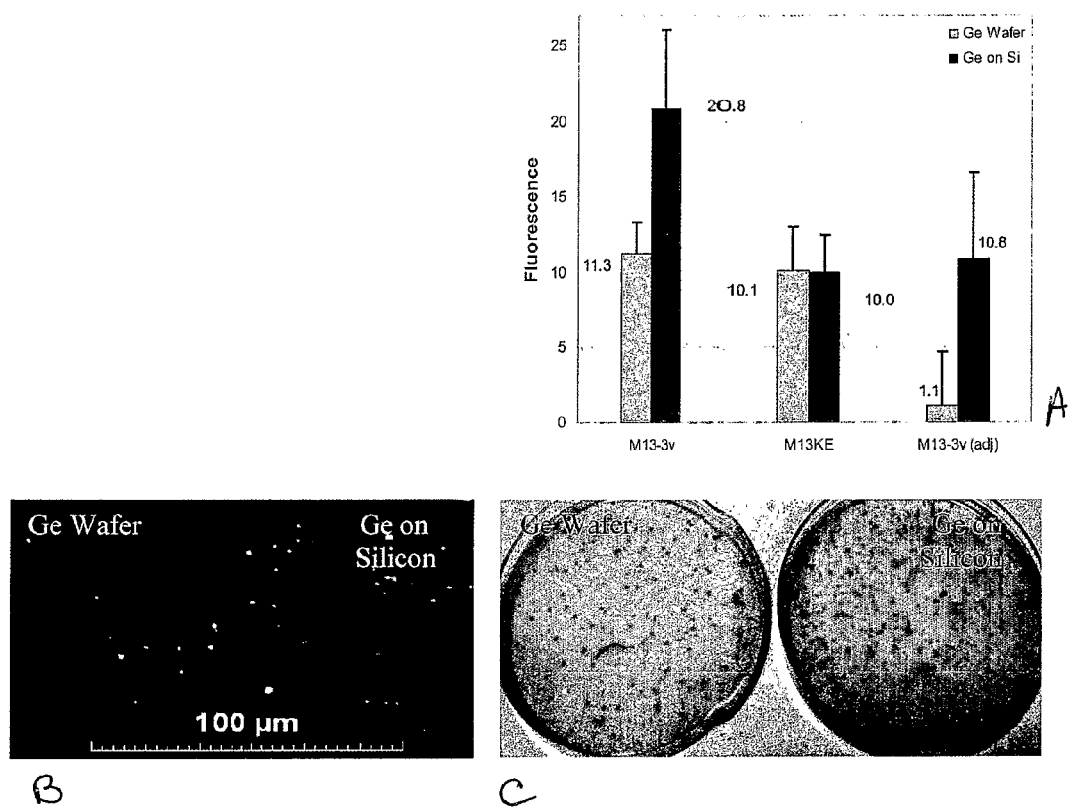
FIG. 3A is a graph illustrating the fluorescence of wild-type and 3v M13 phages bound to Ge-on-Si substrates.
FIG. 3B is a contrast enhanced image comparing the fluorescence of wild type and 3v M13 phage bound to Ge-on-Si substrates.
FIG. 3C is an image of two plates produced by a phage titer of M13-3v eluted from Ge and Ge-on-Si substrates.

Once the consensus sequences were identified, we confirmed that they showed a binding preference for surface defects in the Ge-on-Si substrate. Rather than attempting to simultaneously image a micron long virus and a 4 Å surface defect, we used indirect techniques to verify binding. Binding preference between melt grown Ge and Ge-on-Si substrates was determined using fluorescence microscopy and phage titration (FIG. 3). The substrates themselves were also compared. In diffuse selection, we are looking for affinity to a specific target. However, the technique will tend to find whatever differences there are between the two substrates used. To ensure that the most significant difference was the one that was being initially targeted, we examined the elemental composition, surface roughness, crystal orientation, and defect density of the surface.

Fluorescence Measurements

The samples were tagged using streptavidin conjugated tetramethylrhodamine (TMR), which was bound to the major coat protein of the phage using a biotinylated antibody (FIG. 3). The samples were prepared by first cutting the substrates into 5mm×5 mm squares. All the samples were dipped in 48% HF three times for 10 sec each with a water rinse in between. The samples were then dipped in 0.07% $HNO_3$ for 10 sec and rinsed again. The samples then received 2× rinse in acetone, 2× rinse in ethanol and a final rinse in acetone. The samples were then arranged in a 2×2 array and exposed to 20Φl/sample of phage solution ($10^6$ phage/Φl; determined by titration and spectrometric analysis[16]). After half an hour, the samples received an intermediate wash (1× TBST-BSA [TBS+0.5 g/L BSA+0.5% Tween-20], 1× TBST [TBS+0.2% Tween-20], 1× 10% TBS). The samples were then exposed to 20Φl/sample of biotinylated anti-fd (1:50 dilution of stock solution, Sigma) for half an hour. After a second intermediate wash, samples were finally exposed to 20Φl/sample of streptavidin-conjugated TMR (1:100 dilution of stock solution, Molecular Probes). The samples then received a final wash (4× TBST-BSA [TBS+0.5 g/L BSA+0.5% Tween-20], 4× TBST [TBS+0.2% Tween-20], 1× 10% TBS, 1× $H_2O$) and were mounted and measured. The fluorescence measurements were made using a TRITC filter on an Olympus IX51 fluorescence microscope. Images were taken of the samples using an Olympus Q-Color 3 CCD, and their average luminescence was determined using a standard software suite (Adobe Photoshop 6.0: Histogram function).

Titration

The samples were prepared using the same steps as in the fluorescence measurement except that, after the phage exposure, the samples received the final wash in lieu of the anti-fd and TMR exposure. The phage were then eluted and titered as described in the manual for the New England Biosciences phage display kit, the contents of which are incorporated herein by reference. The results of the titration are plates with blue viral plaques. The number of plaques corresponds to the number of phage that bound the substrate. The viral population is diluted before plating so that the number of plaques on a given plate can be counted by hand.

XPS Measurements

XPS was done using a small spot ESCA with an Al source and a pass energy of 187.85 eV. The binding energy was swept from 0 to 1300 eV.

AFM Measurements

Figure 4:
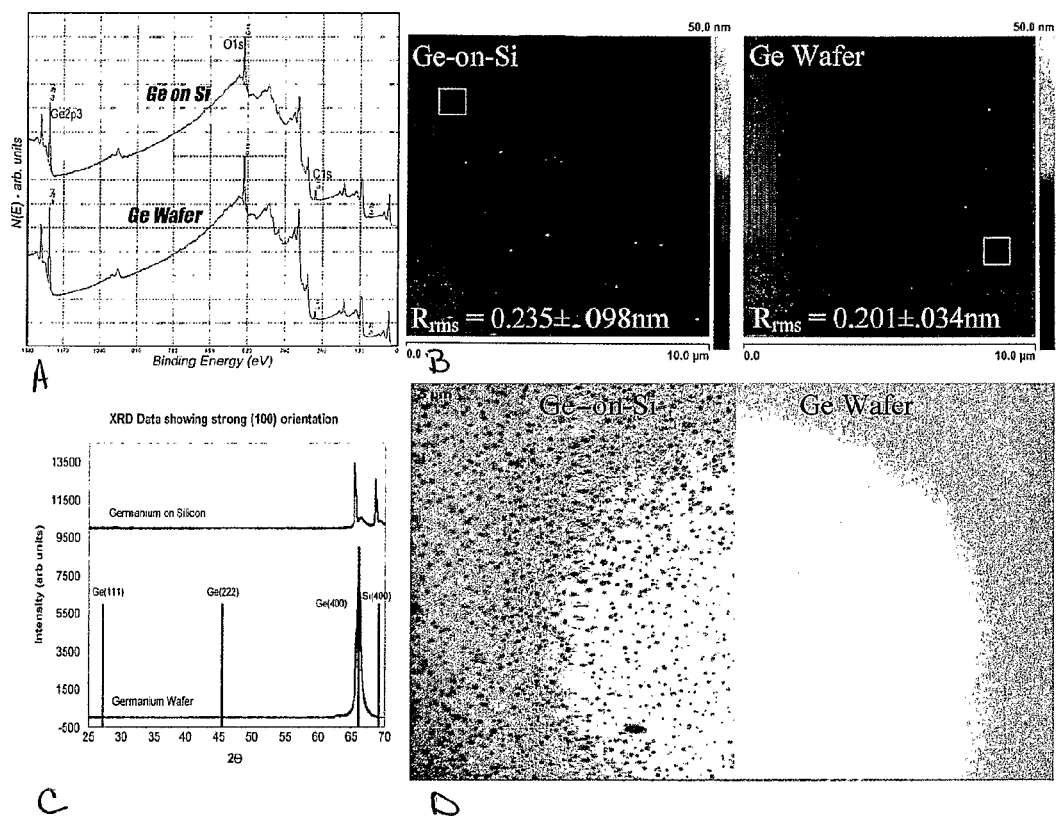
FIG. 4A is a graph showing XPS data for a Ge and Ge-on-Si surface.
FIG. 4B includes AFM images of Ge and Ge-on-Si surfaces.
FIG. 4C is a graph showing XRD spectra for Ge and Ge-on-Si surfaces.
FIG. 4D includes photographs of Ge-on-Si and Ge surfaces after EPD.

AFM was done using a Digital Instruments Nanoscope 4. Spot sizes approximately 1 micron on a size were used with a built in roughness measurement protocol (FIG. 4).

XRD Measurements

XRD was done using a Cu Kα source. The 2Θ angle was swept from 25° to 70°.

EPD Measurement

The etchant included 67 ml $CH_3COOH$, 20 ml $HNO_3$, 10 ml HF, and 30 mg $I_2$. The samples were dipped for 10 sec and then imaged using an Olympus optical microscope. (FIG. 4)

Results

The 3v sequence occurred with the highest frequency during sequencing, and characterization focused on that peptide. Fluorescence measurements were performed using two distinct phage populations. One population was a monodisperse collection of viral clones all expressing 3v (M13-3v). The second population was made up of the 'wild-type' phage known as M13KE, which lack the peptide fusion on pIII but are otherwise identical to M13-3v, thus providing a good control for the effect of non-selective background binding. The phage were fluorescently tagged using an antibody for the phage (biotinylated anti-fd) which is linked to a fluorescent dye (streptavidin-conjugated TMR) via the biotin-streptavidin linkage (FIG. 3). A background control was obtained by repeating the method with a phage free sample containing just biotin-conjugated anti-fd and streptavidin-conjugated TMR. Overall, there are four potential contributions to background fluorescent signal: 1) any noise experienced by the CCD during exposure, 2) any non-selective antibody/dye binding to the substrate, 3) any non-selective binding of the large viral assembly, and 4) any germanium affinity that the selected peptide may have. The first two contributions were small and simply subtracted from the measured fluorescence. The resulting M13-3v fluorescence measurements revealed a roughly 2:1 preference for the Ge-on-Si substrate compared to the Ge substrate (FIG. 3A). The fluorescence signal resulting from M13KE binding showed no selectivity for either substrate and was slightly smaller than the signal due to M13-3v on Ge. When the M13KE binding is treated as background to the M13-3v binding, the Ge-on-Si to Ge preference increases to 10:1 (FIG. 3).

Titration is a quantitative technique for measuring the number of phage that bind a substrate. After substrate exposure and before amplification, a fraction of the eluted phage population is exposed to a bacterial lawn that has been grown on culture plates. At each point where the bacterial lawn becomes infected, a viral bloom forms. The phage are modified with a lacZ, causing the viral bloom (or 'plaque') to turn blue. If the phage are sufficiently diluted, each plaque corresponds to only one infection event. By counting the number of plaques on a given plate at a given dilution, it is possible to determine the number of phage that bound the original substrate. Titration measurements were made using the monodispersed M13-3v phage population (these results were not compared to the wild type M13KE because wild type phage show a higher rate of infectivity). No antibody or fluorescent dye was needed for titration. The resulting plates indicated a 3:1 preference for the Ge-on-Si substrate compared to the Ge substrate (FIG. 3C), which is similar to the 2:1 seen in fluorescence.

The fluorescence and titration results confirm that M13-3v exhibits a preference for Ge-on-Si. We also demonstrated that the Ge and Ge-on-Si surfaces were identical except for the presence of dislocations. XPS data revealed that the substrates had the same elemental composition (FIG. 4A). AFM images demonstrated that the substrates are quite smooth, with similar surface roughnesses (Ge-on-Si: $R_{rms}$=0.235+/−0.098 nm; Ge wafer: $R_{rms}$=0.201+/−0.034 nm) (FIG. 4B). XRD indicated that the substrates both have a strong (100) orientation (FIG. 4C). Finally, EPD testing revealed that there were numerous defects in the Ge-on-Si substrate and none in the Ge wafer (FIG. 4D). The intermediate density samples had approximately $2^7/cm^2$ disclocations, while the pure germanium samples had $1^3/cm^2$. The high dislocation density samples had dislocations that were too densely packed to differentiate using EPD. As a result, the value of $1^9/cm^2$ was used as a typical value for this type of structure.

Conclusion

The two peptide sequences derived from the phage display selection were quite similar. The odds of this level of similarity occurring by chance are roughly 0.02% (assuming all amino acids were independent and equally likely). This is extremely encouraging as the sequences were essentially arrived at independently. This level of overlap gives confidence that we were able to focus on the proper space of possible binding sequences. This assertion is also supported out by the fluorescence and titration data.

The mechanism for binding is not entirely clear. Without being bound by any particular theory, we hypothesize that there is likely a space charge region associated with the surface defects. This could be the source of a primarily electrostatic interaction. However, the germanium film is nominally undoped (slightly p-type, $N_A$~$10^{16}/cm^{3\ 16}$) so the magnitude of the space charge would be quite small and spread out. The binding mechanism may also derive from the local chemistry of the defect. We expect that the site of a dislocation will oxidize preferentially. It has been shown that hydroxyl containing amino acids will bind to metal oxides[17].

In an effort to quantify the phage binding, a basic model was developed. The phage-surface interactions are treated as simple bimolecular interactions.

For the phage-dislocation interaction, we have:

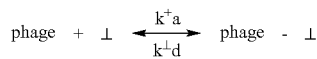

For the phage-background interaction, we have:

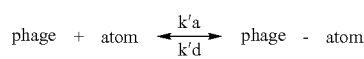

At equilibrium we have:

$$K_D^\perp = k_d/k_a = \frac{[phage][\perp]}{[phage-\perp]}$$

$$K_D' = k_d'/k_a' = \frac{[phage][atom]}{[phage-atom]}$$

where $K_D$ are equilibrium dissociation constants. Because the complimentary substrates were exposed to the same phage solution simultaneously, [phage] is the same for both samples. Additionally, because the whole sample surface is exposed to the phage solution, [phage] is the same for defects and background. Solving for [phage] and rearranging:

$$\frac{K_D'[phage-atom]}{[atom]} = \frac{K_D^\perp[phage-\perp]}{[\perp]}$$

If the Ge-on-Si fluorescence is twice the Ge wafer fluorescence (assuming [phage-atom] is the same on either substrate), then:

[phage-atom]=[phage-$\perp$]

Substituting and canceling:

$$K_D'/[atom] = K_D^\perp/[\perp]$$

Note that the atomic surface density is roughly $10^{14}/cm^2$ while the dislocation density is $10^9/cm^2$. As a result, $$\rightarrow [atom]/[\perp] = 10^5$$
$$\therefore K_D^\perp/K_D' = 10^{-5}$$

Substituting this into equation (7) yields:

$$\therefore K_D^\perp/K_D' = 10^{-5}$$

That is, there is effectively a 100,000-fold improvement in selectivity.

Example 3

Development of Phage Population Selective for Doped Silicon

Two types of silicon wafers are provided: undoped silicon and undoped silicon including one or more doped regions prepared using methods known to those skilled in the art, for example, ion implantation. The two wafers are etched with HF to remove the native oxide layer and stored under dry nitrogen. A phage display library exhibiting variation in either the pIII or pVIII coat protein is exposed to the silicon wafer with the doped regions ("doped silicon wafer") in an inert atmosphere, for example, in a glove box. After about an hour, the wafer is washed with buffer, and the bound phage are eluted from the wafer with 0.2M glycine HCl. The incubation is repeated with the recovered phage, but using 0.2% Tween-20 in buffered saline to wash the unbound phage from the surface.

The phage recovered after the second incubation are amplified using *E. Coli* according to standard microbiological techniques, for example, using the techniques in the New England Biolabs Manual, the contents of which are incorporated herein by reference. The amplified phage population is incubated with the undoped silicon wafer for about an hour, following which the silicon wafer is washed with buffer and the unbound phage recovered (e.g., the phage remaining on the silicon wafer are discarded).

The recovered phage are incubated with a doped silicon wafer for about an hour. The wafer is washed with 0.5% Tween-20 in buffer. The phage are eluted from the wafer using glycine HCl as above and the eluted phage sequenced. If more than one sequence appears with about the same frequency, the above steps may be repeated, using a mixture of phage exhibiting peptides having one of the selected sequences and stronger concentrations of detergent.

A population of phage displaying the doped silicon-selective peptide is prepared. The phage are fluorescently labeled and incubated with a doped silicon wafer. Fluorescence microscopy of the wafer is used to confirm that the phage are bound to the doped regions of the wafer.

Example 4

Detection of A-Axis Oriented Grains in Yttrium Bismuth Copper Oxide Films

A population of phage selective for a-axis oriented grains with respect to c-axis oriented grains of $YBa_2Cu_3O_7$ (YBCO) is tagged with a fluorescent label and suspended in buffered saline to a concentration of $10^{12}$ phage/µL. A segment of YBCO tape is cleaned using a mild soap and water and, if necessary, polished to remove visible scratches. The phage/buffer suspension is disposed on the YBCO tape, for example, by spraying the tape with a pump-action spray bottle or by immersing the segment of tape in the suspension. The tape is then washed with a mild soap and fluorescence imaging employed to locate the bound phage on the surface, corresponding to a-axis oriented grains. Where the tag absorbs red light, for example, and fluoresces at a visible wavelength, a handheld laser may be used to stimulate the fluorescence and visualize the a-axis grains.

Example 5

Detection of Grain Boundaries in a Polycrystalline Material

A population of phage selective for grain boundaries of a polycrystalline material is tagged with a radioactive label and suspended in buffered saline to a concentration of $10^{12}$ phage/µL. A component fabricated from the polycrystalline material is polished using a handheld mechanical sander and sprayed with the phage/buffer suspension. After about an hour, the component is washed with a detergent, e.g., 0.2% Tween-20 in buffered saline, and the radioactive emission from the component is photographed. This procedure may be repeated at intervals, e.g., every month or every quarter, to monitor grain coarsening in the component.

Example 6

Figure 5:
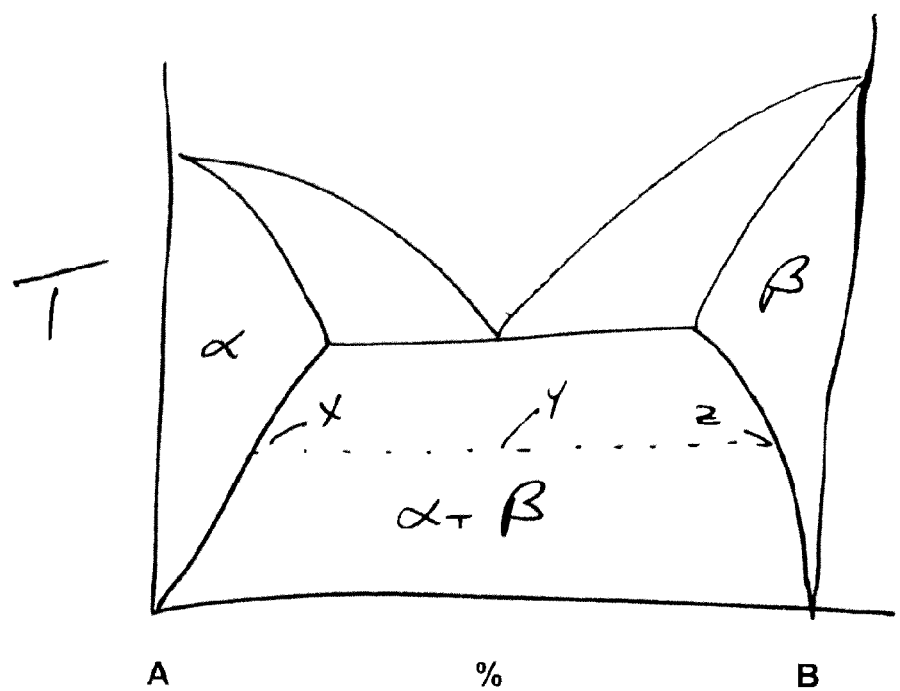
FIG. 5 is a phase diagram for a hypothetical metal alloy.

Identification of a Phage Population Selective for Alloys of a Particular Composition Two alloys of A and B are prepared having compositions X and Z (FIG. 5). Samples of these alloys are polished to remove visible scratches and stored under nitrogen. A phage display library exhibiting variation in either the pIII or pVIII coat protein is exposed to the Z sample. After about an hour, the sample is washed with buffered saline, and the bound phage are eluted from the sample with glycine HCl.

The recovered phage are incubated with the X sample for about an hour. The unbound phage are washed from the surface with buffered saline, recovered, and amplified. This population is incubated with the X sample. The unbound phage are recovered and incubated with the Z sample. The unbound phage are washed off with detergent and the eluted phage again incubated with sample X. The unbound phage are washed off with a higher concentration detergent, e.g. double the concentration, and the eluted phage amplified. The amplified population is incubated with sample Z and the unbound phage recovered. The recovered phage are incubated with sample X and the eluted phage sequenced.

A population of phage having the X selective peptide fused to one of the coat proteins is provided. The phage are fluorescently labeled and incubated with sample Y. Fluorescence microscopy of the sample is used to confirm that the phage are bound to the Z grains.

Example 7

Identification of a Phage Population Selective for Alloys of a Particular Composition The samples of X and Y discussed in Example 6 are polished and heated in a moist environment to accelerate oxidation. Biopanning is conducted on the oxidized samples as in the Example.

Example 8

Identification of a Phage Population Selective for Areas of Delamination in a Composite A fiber reinforced composite is provided, and a portion of the composite is sectioned or fractured to reveal a surface that includes both the matrix and the reinforcement. A sample of the matrix material is also provided and cleaned with mild detergent. A phage display library exhibiting variation in either the pIII or pVIII coat protein is exposed to the sample of the composite material. After about an hour, the sample is washed with buffered saline, and the bound phage are eluted from the sample with 0.2M glycine HCl.

The eluted phage are incubated with the matrix material for about an hour, following which the sample is washed with buffered saline and the unbound phage recovered and amplified.

The amplified phage are incubated with the composite sample for about an hour. The sample is washed with 0.2% Tween-20 in buffered saline. The phage are eluted from the wafer using glycine HCl as above and the eluted phage incubated with the matrix material. The unbound phage are recovered and incubated with the composite sample, which is then washed with a higher concentration, e.g., 0.4%, of Tween-20. The eluted phage are sequenced to reveal the sequences selective for the reinforcement material.

A population of phage having the reinforcement-selective peptide fused to one of the coat proteins is prepared. The phage are fluorescently labeled and incubated with a composite sample. Fluorescence microscopy of the sample is used to confirm that the phage are bound to the reinforcement material.

Example 9

Detection of Corrosion Pits on a Steel Sample

A population of phage selective for iron oxide with respect to chromia, metallic iron, or both is tagged with a fluorescent label and suspended in buffered saline to a concentration of $10^{12}$ phage/µL. A portion of a steel item to be evaluated is cleaned with a detergent and optionally with a solvent such as acetone, kerosene, or trifluoroethylene. The phage/buffer suspension is sprayed on the clean surface and allowed to incubate for about an hour. The surface is then washed with a mild soap and fluorescence imaging employed to locate the bound phage on the surface, corresponding to corrosion pits in the metal.

Example 10

Repair of a Pinhole Defect

A peptide including a sequence selective for polystyrene with respect to nickel is prepared using solid phase peptide synthesis techniques and functionalized with an alkanethiol. The functionalized peptide is allowed to attach to 40 nm gold nanoparticles in solution and the peptide-nanoparticle conjugates recovered. The conjugates are suspended in buffered saline and incubated on a nickel-plated polystyrene surface for about two hours and then rinsed with buffer. The surface is then incubated with a commercial electroless nickel plating solution according to the manufacturer's directions.

REFERENCES (1) Belcher, A. M., Wu, X. H., Christensen, R. J., Hansma, P. K., Stucky, G. D., Morse, D. E. *Nature* 1996, 381, 56-58.
(2) Flynn, C. E., Mao, C., Hayhurst, A., Williams, J. L., Georgiou, G., Iverson, B., Belcher, A. M. *J. Mater. Chem.* 2003, 13, 2414-2421.
(3) Mao, C. B.; Solis, D. J.; Reiss, B. D.; Kottmann, S. T.; Sweeney, R. Y.; Hayhurst, A.; Georgiou, G.; Iverson, B.; Belcher, A. M. *Science* 2004, 303, 213-217.
(4) Lee, S.-W., Mao, C., Flynn, C. E., Belcher, A. M. *Science* 2002, 296.
(5) Seeman, N. C., Belcher, A. M. *PNAS* 2002, 99, 6451-6455.
(6) Alivisatos, A. P.; Johnsson, K. P.; Peng, X. G.; Wilson, T. E.; Loweth, C. J.; Bruchez, M. P.; Schultz, P. G. *Nature* 1996, 382, 609-611.
(7) Mirkin, C. A.; Letsinger, R. L.; Mucic, R. C.; Storhoff, J. J. *Nature* 1996, 382, 607-609.
(8) Whaley, S. R.; English, D. S.; Hu, E. L.; Barbara, P. F.; Belcher, A. M. *Nature* 2000, 405, 665-668.
(9) Rosner, S. J.; Girolami, G.; Marchand, H.; Fini, P. T.; Ibbetson, J. P.; Zhao, L.; Keller, S.; Mishra, U. K.; DenBaars, S. P.; Speck, J. S. *Applied Physics Letters* 1999, 74, 2035-2037.
(10) Giovane, L. M.; Luan, H. C.; Agarwal, A. M.; Kimerling, L. C. *Applied Physics Letters* 2001, 78, 541-543.
(11) Deegan, T.; Hughes, G. *Applied Surface Science* 1998, 123, 66-70.
(12) Colace, L.; Masini, G.; Assanto, G.; Luan, H. C.; Wada, K.; Kimerling, L. C. *Applied Physics Letters* 2000, 76, 1231-1233.
(13) Luan, H. C.; Lim, D. R.; Lee, K. K.; Chen, K. M.; Sandland, J. G.; Wada, K.; Kimerling, L. C. *Applied Physics Letters* 1999, 75, 2909-2911.
(14) Gan, S.; Li, L.; Hicks, R. F. *Applied Physics Letters* 1998, 73, 1068-1070.
(15) Kruml, T.; Caillard, D.; Dupas, C.; Martin, J. L. *Journal of Physics-Condensed Matter* 2002, 14, 12897-12902.
(16) Barbas, C. F.; Burton, D. R.; Scott, J. K.; Silverman, G. J. In *Phage Display: A Laboratory Manual,* 1st ed.; Cold Spring Harbor Laboratory Press, 2001; pp 15.17-15.18.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A composition comprising one or more peptides,
wherein the one or more peptides comprise a sequence that binds a target feature A of a material B, and the one or more peptides do not bind B in the absence of A;
wherein A comprises at least one of a surface defect and an impurity;
wherein the sequence is CTSPHTRAC (Seq ID: 2).

2. The composition of claim 1, wherein A comprises at least one of a grain boundary and a dislocation.

3. The composition of claim 1, wherein A comprises at least one of a grain of an alloy having an equilibrium composition, a grain of a mixture of two or more metals having an equilibrium composition, a grain of a mixture of two or more ceramics having an equilibrium composition, a grain of an alloy having a non-equilibrium composition, a grain of a mixture of two or more metals having a non-equilibrium composition, a grain of a mixture of two or more ceramics having a non-equilibrium composition, and a doped semiconductor material.

4. The composition of claim 1, wherein A comprises at least one of a reinforcement material, a corrosion scale having a different composition than B, a corrosion pit, and a substrate material.

5. The composition of claim 1, wherein:
A comprises a grain boundary, and
B comprises a polycrystalline material.

6. The composition of claim 1, wherein:
A comprises a dislocation, and
B comprises a crystalline material.

7. The composition of claim 1, wherein:
A comprises a grain having an equilibrium or a non-equilibrium composition, and
B comprises an alloy, a mixture of two or more metals, or a mixture of two or more ceramics.

8. The composition of claim 1, wherein:
A comprises a doped semiconductor material, and
B comprises a semiconductor material.

9. The composition of claim 1, wherein:
A comprises a reinforcement material, and
B comprises a composite; wherein the composite comprises a matrix material and the reinforcement material.

10. The composition of claim 1, wherein:
A comprises a corrosion scale with a first composition, and
B comprises a corrosion scale with a second composition;
wherein the first composition is different from the second composition.

11. The composition of claim 1, wherein:
A comprises a corrosion pit, and
B comprises an optionally passivated metal.

12. The composition of claim 1, wherein:
A comprises a substrate material, and
B comprises a coating material disposed on the substrate material.

13. The composition of claim 1, wherein the one or more peptides are part of a virus.

14. The composition of claim 1, wherein the one or more peptides are linked to a fluorescent, radioactive, or magnetic label.

15. A composition comprising a peptide, wherein the peptide:
selectively binds a screw dislocation of a single crystalline germanium material,
does not bind the single crystal germanium material in the absence of the screw dislocation, and
has the sequence CTSPHTRAC (Seq ID: 2).

16. The composition of claim 15, wherein the single crystalline germanium material is disposed over a silicon wafer.

17. The composition of claim 15, wherein the peptide is a part of a virus.

18. The composition of claim 15, wherein the peptide is linked to a fluorescent, radioactive, or magnetic label.

19. The composition of claim 1, wherein:
A comprises a grain having a suboptimal orientation, and
B comprises an alloy, a mixture of two or more metals, or a mixture of two or more ceramics.

20. The composition of claim 1, wherein:
A comprises a delamination of a matrix material and a reinforcement material, and
B comprises a composite; wherein the composite comprises the matrix material and the reinforcement material.

* * * * *

UNITED STATES PATENT AND TRADEMARK OFFICE
CERTIFICATE OF CORRECTION

| | | |
|---|---|---|
| PATENT NO. | : 8,592,551 B2 | Page 1 of 1 |
| APPLICATION NO. | : 11/912043 | |
| DATED | : November 26, 2013 | |
| INVENTOR(S) | : Sinensky et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1822 days.

Signed and Sealed this
Twenty-first Day of April, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: consensus sequence

<400> SEQUENCE: 1

Cys Ser Tyr His Arg Met Ala Thr Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Consensus sequence

<400> SEQUENCE: 2

Cys Thr Ser Pro His Thr Arg Ala Cys
1               5
```